United States Patent
Lisogurski

(10) Patent No.: US 10,765,375 B2
(45) Date of Patent: Sep. 8, 2020

(54) PHYSIOLOGICAL MONITORING METHODS AND SYSTEMS UTILIZING FILTER SCALING

(71) Applicant: Covidien LP, Mansfield, MA (US)

(72) Inventor: Daniel Lisogurski, Boulder, CO (US)

(73) Assignee: COVIDIEN LP, Mansfield, MA (US)

( * ) Notice: Subject to any disclaimer, the term of this patent is extended or adjusted under 35 U.S.C. 154(b) by 726 days.

(21) Appl. No.: 15/354,863

(22) Filed: Nov. 17, 2016

(65) Prior Publication Data

US 2017/0143277 A1   May 25, 2017

Related U.S. Application Data

(60) Provisional application No. 62/258,233, filed on Nov. 20, 2015.

(51) Int. Cl.
| | | |
|---|---|---|
| A61B 5/00 | (2006.01) | |
| A61B 5/1455 | (2006.01) | |
| A61B 5/0205 | (2006.01) | |
| A61B 5/1495 | (2006.01) | |
| A61B 5/024 | (2006.01) | |

(52) U.S. Cl.
CPC .......... *A61B 5/7225* (2013.01); *A61B 5/0205* (2013.01); *A61B 5/1495* (2013.01); *A61B 5/14551* (2013.01); *A61B 5/725* (2013.01); *A61B 5/7207* (2013.01); *A61B 5/742* (2013.01); *A61B 5/02416* (2013.01); *A61B 2560/0214* (2013.01)

(58) Field of Classification Search
CPC ... A61B 5/7225; A61B 5/0205; A61B 5/1495; A61B 5/7207; A61B 5/725; A61B 5/742; A61B 5/02416; A61B 2560/0214
See application file for complete search history.

(56) References Cited

U.S. PATENT DOCUMENTS

| | | | |
|---|---|---|---|
| 4,819,752 A | 4/1989 | Zelin | |
| 4,851,841 A * | 7/1989 | Sooch | H03M 3/488 |
| | | | 341/143 |
| 5,193,543 A | 3/1993 | Yelderman | |
| 5,921,921 A * | 7/1999 | Potratz | A61B 5/14551 |
| | | | 600/323 |
| 6,731,967 B1 | 5/2004 | Turcott | |

(Continued)

*Primary Examiner* — Eric F Winakur
*Assistant Examiner* — Abid A Mustansir
(74) *Attorney, Agent, or Firm* — Cantor Colburn LLP

(57) ABSTRACT

Systems and methods are provided for operating a physiological monitoring system for determining a physiological parameter of a subject. The physiological system may comprise a pulse oximetry sensor for generating a photoplethysmography (PPG) signal and a gain controller for setting a light detection level. The system may also comprise a filter for filtering the PPG signal. The filter may comprise at least one of filter history and filter coefficients. The system may comprise a processor for determining the power level of light sources of the pulse oximetry sensor and the light detection gain level, and calculating a scaling factor based on the determined power level and the light detection gain level. The processor may also be used for scaling one or more of the filter history and filter coefficients based on the scaling factor, and determining at least one physiological parameter based on the filtered PPG signal.

18 Claims, 6 Drawing Sheets

(56) References Cited

U.S. PATENT DOCUMENTS

| | | | |
|---|---|---|---|
| 7,190,985 B2* | 3/2007 | Petersen | A61B 5/14551 |
| | | | 600/322 |
| 7,738,935 B1 | 6/2010 | Turcott | |
| 7,840,246 B1 | 11/2010 | Poore | |
| 2009/0237280 A1* | 9/2009 | Ashmore, Jr. | H03M 3/382 |
| | | | 341/120 |
| 2009/0326335 A1* | 12/2009 | Baker | A61B 5/02416 |
| | | | 600/300 |
| 2013/0324856 A1* | 12/2013 | Lisogurski | A61B 5/7285 |
| | | | 600/476 |
| 2014/0323876 A1* | 10/2014 | McGonigle | A61B 5/7225 |
| | | | 600/476 |

* cited by examiner

PHYSIOLOGICAL MONITORING METHODS AND SYSTEMS UTILIZING FILTER SCALING

CROSS-REFERENCE TO RELATED APPLICATION

This application claims the benefit of U.S. Provisional Application No. 62/258,233, filed Nov. 20, 2015, which is hereby incorporated by reference herein in its entirety.

BACKGROUND

The present disclosure relates to generating and processing signals in a physiological monitoring system, and more particularly to techniques for scaling filter histories or filter coefficients to attenuate filter artifacts in a received signal to improve the determination of physiological parameters by the physiological monitoring system.

Photoplethysmography (PPG) is a non-invasive, optical measurement that may be used to detect changes in blood volume within tissue of an individual. PPG signals may be used by pulse oximeters, vascular diagnostics system, and digital blood pressure detection systems. Typically, a PPG system includes a light source that is used to illuminate tissue of a patient and a photodetector that is used to detect light attenuated by the tissue of a patient. A PPG system may analyze variations in the detected light intensity that may be associated with blood volume changes proximal to the illuminated tissue. The analysis may be used to determine physiological parameters of the individual.

PPG systems often utilize a variety of filters to condition or process the output of the photodetector. Some filters comprise a filter history or filter coefficients. For example, the output of digital Finite Impulse Response (FIR) filters may be determined by filter coefficients and a history of previous input samples. The output of digital Infinite Impulse Response (IIR) filters may also depend on a history of previous outputs from the filter. During normal operation, a PPG system may adjust the intensity of the light source and change settings of gain circuitry or ambient light cancellation circuitry that processes the photodetector signal in order to amplify the signal. These adjustments may be performed in order to increase the signal-to-noise ratio, to avoid saturating an ADC (analog-to-digital converter) of the PPG system, or to save power when driving light emitters or for a number of other reasons. Changes to light intensity, gain or ambient light rejection may occur very frequently when emitters are dynamically adjusted within a cardiac cycle to save power. Some exemplary techniques for changing light intensity are disclosed in U.S. Patent Application Publications Nos.: 2013/0324809, 2013/0324855, 2013/0324856, and 2015/0173687, which are hereby incorporated by reference. In some embodiments, the filters may experience an effect similar to an effect produced by a change in emitter drive current of a system that changes emitter wavelengths. Such effects are described, for example, by U.S. Pat. No. 8,649,838, which is hereby incorporated by reference. When these adjustments in light detection gain or in light intensity occur, the filter history may simultaneously include photodetector signal samples acquired at the old level of the photodetector signal and the new level of the photodetector signal. In addition, filtering coefficients may be applied simultaneously to the old level of the photodetector signal and the new level of the photodetector signal. Such simultaneous processing can introduce filter artifacts (e.g., a step response) into the photodetector signal. These filter artifacts may negatively affect determination of physiological parameters by the PPG system.

Accordingly, the present specification discloses improved systems and methods for determining physiological parameters based on a PPG signal, where the filter history and/or the filter coefficients are scaled based on adjustments to the intensity of one or more light sources and adjustments to the settings of gain controller or ambient light cancellation circuitry in a manner designed to eliminate or attenuate filter artifacts. The disclosed systems and methods improve the operation of a PPG system by eliminating or attenuating filter artifacts that may introduce errors into algorithms for determining physiological parameters (e.g., heart rate, oxygen saturation, respiration rate, and regional oxygen saturation).

SUMMARY

The present disclosure is generally directed towards systems and methods for determining physiological parameters. In some embodiments, a physiological monitoring system (e.g., a medical device such as a pulse oximeter) may comprise a sensor configured to detect light attenuated by a subject and generate a photoplethysmography (PPG) signal. The physiological monitoring system may also comprise a gain controller configured to set a light detection gain level. The system may also comprise a filter for filtering the PPG signal. The filter may comprise at least one of filter history and filter coefficients. The physiological monitoring system may also comprise a processor for determining at least one of the power level of one or more light sources of the pulse oximetry sensor and the light detection gain level. The processor may also be used for calculating a scaling factor based on at least one of the determined power level and determined gain level and scale one or more of the filter history and the filter coefficients using the scaling factor. The processor may also be used for determining a physiological parameter based on the PPG signal that was filtered by the filter. The system may comprise a display configured to display the physiological parameter of the subject or a wired or wireless communication interface such as a UART, SPI, WiFi or Bluetooth interface for communicating the physiological parameter to another system.

In some embodiments, a method is provided for determining physiological parameters of a subject using a pulse oximeter. The method may comprise generating, using a pulse oximetry sensor, a photoplethysmographic (PPG) signal. The pulse oximetry sensor may be configured to detect light attenuated by the subject. The method may also comprise setting a light detection gain level using a gain controller. The method may also comprise filtering the PPG signal using a filter. The filter may comprise at least one of filter history and filter coefficients. The method may further comprise determining, using a processor of the pulse oximeter, at least one of the power level and the gain level. The method may further comprise calculating a scaling factor based on the at least one of the determined power level and determined gain level, and scaling one or more of the filter history, the filter coefficients, and the filter input samples using the scaling factor. The method may further comprise determining a physiological parameter based on the PPG signal that was filtered by the filter. The method may further comprise displaying, using a display of the pulse oximeter, the physiological parameter of the subject.

BRIEF DESCRIPTION OF THE FIGURES

The above and other features of the present disclosure, its nature and various advantages will be more apparent upon consideration of the following detailed description, taken in conjunction with the accompanying drawings in which.

DETAILED DESCRIPTION OF THE FIGURES

Figure 1:
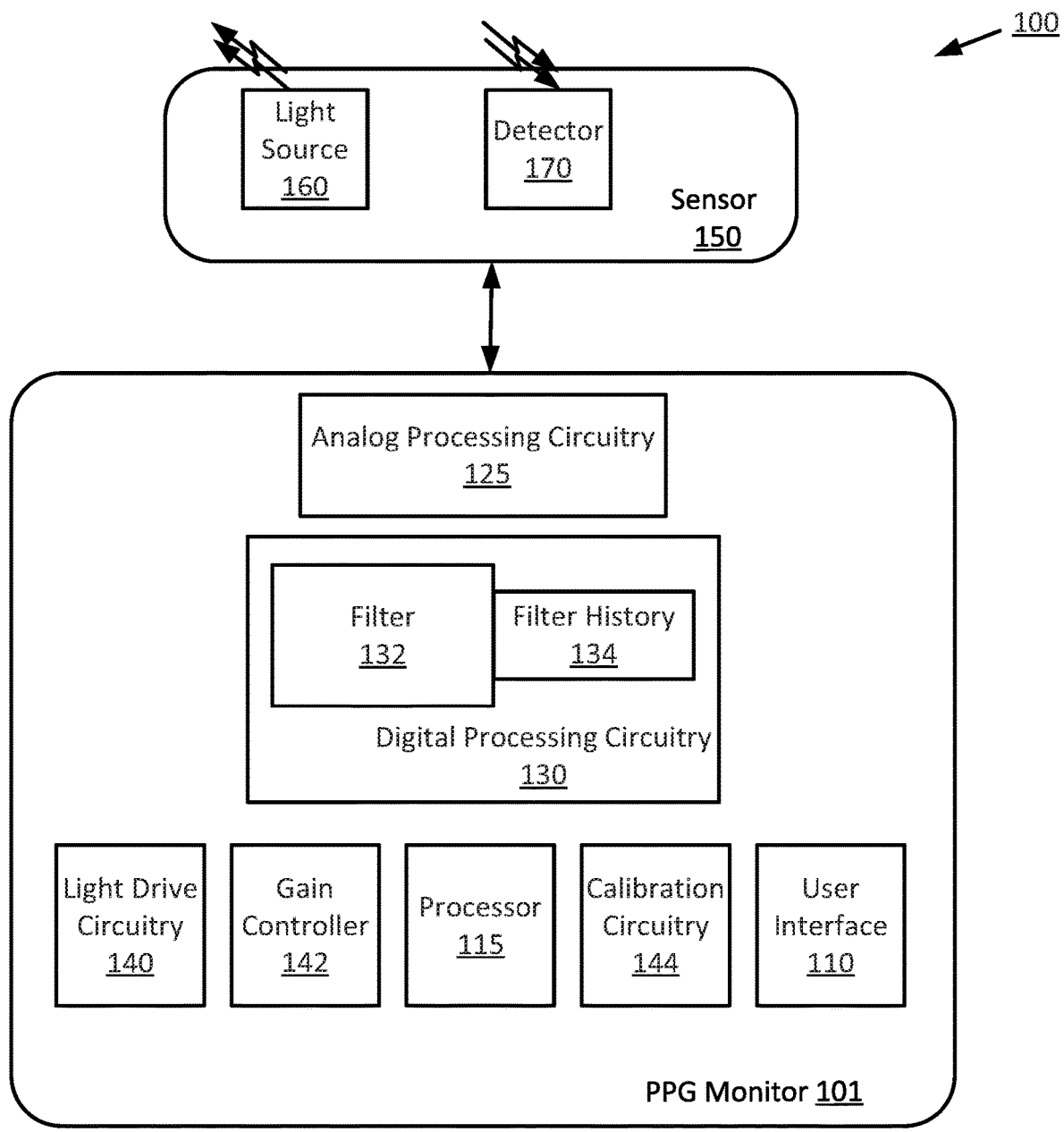
FIG. 1 shows a block diagram of an illustrative system for determining a physiological parameter in accordance with some embodiments of the present disclosure.

The systems and methods described below may be implemented using a physiological monitoring system, such as an oximeter or any other type of PPG system. In some embodiments, the PPG device may comprise a monitor and a sensor that may be commutatively coupled to the monitor. The sensor may be configured to generate a PPG signal and transmit the signal to the physiological monitor. The physiological monitor may comprise an oximetry front end and oximetry back end for processing the PPG. In some embodiments, the physiological monitor may comprise light drive circuitry for providing power to a light source of the sensor. In some embodiments, the physiological monitor may comprise a gain controller for setting a gain level of the physiological monitor and for removing the effects of ambient light. In some embodiments, the physiological monitor may comprise analog processing circuitry and digital processing circuitry. Analog processing circuitry may comprise configurable filters (e.g., filter circuitry). Digital processing circuitry may also comprise a filters for filtering the PPG signal. In some embodiments, each of filters may comprise one or more of filter history and filtering coefficients. The physiological monitor may comprise a processor configured to determine an emitter power level and a gain level. The processor may also calculate a scaling factor based on the power level and the gain level. The processor may be configured to scale filter history and/or filtering coefficients of the digital processing circuitry, thus attenuating or eliminating filtering artifact associated with the changes in power and gain levels. The processor may be configured to adjust filtering performed by the analog processing circuitry to attenuate or eliminate filtering artifact associated with the changes in power and gain levels. The digital processing circuitry may then filter the PPG signal using scaled filter histories or filtering coefficients. The PPG system may then determine a physiological parameter based on the filtered PPG signal.

For purposes of this disclosure, "filter" may refer to any hardware component (e.g., processor, controller, filter circuitry, non-transitory memory) or a combination of hardware (including any associated filter circuitry) and software configured to perform signal filtering operations. For example, a filter may be configured to apply filtering to an input signal and produce a filtered output. A filter may be configured to perform analog filtering, digital filtering, any other filtering, or any combination thereof.

For purposes of this disclosure, "filter history" may refer to any circuit (including, e.g., non-transitory memory), data structure, hardware component (e.g., processor, controller), software component, firmware component, or any combination thereof, for storing values that were calculated or used by a filter at any time in the past. In some embodiments, filter history may include a data segment that is currently being processed by the filter. In some embodiments, filter history may include the prior output of the filter.

For purposes of this disclosure, "filter coefficients" may refer to values stored by any circuit (including, e.g., non-transitory memory), data structure, or any combination thereof, for use by a filter. In some embodiments, filter coefficients may be applied to the signal by a filter to produce a filtered signal.

For purposes of this disclosure, "gain controller" may refer to any gain circuitry, gain circuits (including, e.g., a programmable gain array, a current-to-voltage converter, and an analog-to-digital converter), hardware component, combination of hardware and software components, or any combination thereof that is configured to adjust or change the gain of signal received from a sensor. For example, a gain controller may be configured to adjustably amplify a signal received from a sensor.

For purposes of this disclosure, "gain change" may refer to a change in the gain of the system or to a change in power level, duty cycle, or drive pattern of one or more light sources. In some embodiments, drive pattern may comprise PWM modulation. For example, gain change may also refer to a change to at least one variable hardware gain stage, a change in hardware integration time, a change to any ambient light cancellation including DAC subtraction, a change in emitter wavelength (e.g., a change to driving a 735 nm LED instead of a previously driven 660 nm LED), a change in photo-detector location or area such as by combining different photo-detector elements or switching between multiple detectors, combining different elements of a detector array or charge-coupled device (CCD) or other similar adjustments.

As mentioned above, the foregoing techniques may be implemented in an oximeter. An oximeter is a medical device that may determine the oxygen saturation of an analyzed tissue. One common type of oximeter is a pulse oximeter, which may non-invasively measure the oxygen saturation of a subject's blood (as opposed to measuring oxygen saturation invasively by analyzing a blood sample taken from the subject). Pulse oximeters may be included in physiological monitoring systems that measure and display various blood characteristics including, for example, blood oxygen saturation (e.g., arterial, venous, or both). Such physiological monitoring systems, in accordance with the present disclosure, may also measure and display additional or alternative physiological parameters such as pulse rate, respiration rate, respiration effort, blood pressure, hemoglobin concentration (e.g., oxygenated, deoxygenated, and/or total), cardiac output, fluid responsiveness parameters, regional oxygen saturation, any other suitable physiological parameters, or any combination thereof.

An oximeter may include a light sensor that is placed at a site on a subject. For example, the light sensor may be placed on a fingertip, toe, forehead or earlobe, or in the case of a neonate, across a foot or hand. The light sensor may also be placed at any other suitable location on a subject. The oximeter may use a light source to pass light through blood perfused tissue and photoelectrically sense the absorption of the light in the tissue. The oximeter may measure the intensity of light that is received at the light sensor as a function of time. The oximeter may also include sensors at multiple locations. A signal representing light intensity versus time or a mathematical manipulation of this signal (e.g., a scaled version thereof, a log taken thereof, a scaled version of a log taken thereof, an inverted signal, etc.) may be referred to as the photoplethysmography (PPG) signal. In addition, the term "PPG signal," as used herein, may also refer to an absorption signal (i.e., representing the amount of light absorbed by the tissue) or any suitable mathematical manipulation thereof. The light intensity or the amount of light absorbed may then be used to calculate any of a number of physiological parameters.

In some embodiments, the photonic signal interacting with the tissue is of one or more wavelengths that are attenuated by the blood in an amount representative of the blood constituent concentration. Red and infrared (IR) wavelengths may be used because it has been observed that highly oxygenated blood will absorb relatively less red light and more IR light than blood with a lower oxygen saturation. By comparing the intensities of two wavelengths at different points in the pulse cycle, it is possible to estimate the blood oxygen saturation of hemoglobin in arterial blood.

The physiological monitoring system may process data to determine physiological parameters using techniques well known in the art. For example, the physiological monitoring system may determine arterial blood oxygen saturation using two wavelengths of light and a ratio-of-ratios calculation. As another example, the physiological monitoring system may determine regional blood oxygen saturation using two wavelengths of light and two detectors located at different distances from the emitters. The system also may identify pulses and determine pulse amplitude, respiration, blood pressure, other suitable parameters, or any combination thereof, using any suitable calculation techniques. In some embodiments, the physiological monitoring system may use information from external sources (e.g., tabulated data, secondary sensor devices) to determine physiological parameters.

It will be understood that the techniques described herein are not limited to pulse oximeters and may be applied to any suitable physiological monitoring device or any other PPG device.

FIG. 1 shows a block diagram of illustrative physiological monitoring system 100 in accordance with some embodiments of the present disclosure. System 100 may include a sensor 150 and PPG monitor 101 for generating and processing sensor signals (e.g., a PPG signal) that may include physiological information relating to a subject. In some embodiments, sensor 150 and PPG monitor 101 may be part of an oximeter. In some embodiments, system 100 may include more than one sensor. Sensor 150 of physiological monitoring system 100 may include light source 160 and detector 170. PPG monitor 101 may be configured to interface with sensor 150 and perform signal processing of the detector signal received from sensor 150. PPG monitor 101 may comprise light drive circuitry 140, gain controller 142, processor 115, calibration circuitry 144, analog processing circuitry, and digital processing circuitry 130. In some embodiments, light drive circuitry 140 may be a part of processor 115. In some embodiments, gain controller 142 may be a part of processor 115. In some embodiments, calibration circuitry 144 may be a part of processor 115. In some embodiments, digital processing circuitry 130 may be a part of processor 115.

In some embodiments, PPG monitor 101 may be configured to determine physiological parameter of the patient. In some embodiments, PPG monitor 101 may be configured to use processor 115 to determine physiological parameters of the patient. PPG monitor 101 may include user interface 110 configured to display the physiological parameter of the patient and to receive user input.

The components of system 100 are merely illustrative and any suitable components and combinations of components may be used for performing the operations of an oximeter.

Light source 160 of sensor 150 may be configured to emit photonic signals having one or more wavelengths of light (e.g., red and IR) into a subject's tissue. For example, light source 160 may include a red light emitting light source and an IR light emitting light source, e.g., red and IR light emitting diodes (LEDs), for emitting light into the tissue of a subject to generate sensor signals that include physiological information. In one embodiment, the red wavelength may be between about 600 nm and about 750 nm, and the IR wavelength may be between about 800 nm and about 1000 nm. It will be understood that light source 160 may include any number of light sources with any suitable characteristics. In embodiments where an array of sensors is used in place of single sensor 150, each sensor may be configured to emit a single wavelength. For example, a first sensor may emit only a red light while a second may emit only an IR light.

In some embodiments, PPG monitor 101 may comprise light drive circuitry 140 coupled to light source 160. Light drive circuitry 140 may be configured to control the operation of light source 160. In some embodiments, light drive circuitry 140 may generate a light drive signal, which may be used to turn on and off light source 160. Light drive circuitry 140 may also control the intensity of light source 160, for example, by varying the power of the light drive signal. In some embodiments, light drive circuitry 140 may comprise several discrete power level settings for setting the intensity of light source 160. For example, the power level settings may correspond to specific voltages provided to light source 160 or to specific amounts of current provided to light source 160. In some embodiments, the power levels may comprise 4096 discrete levels of electrical current in the range between 0 and 50 mA. In some embodiments, light drive circuitry 140 may control intensity of the light emitted by light source 160 in any other manner. In some embodiments, the overall intensity of the light emitted by light source 160 may be controlled by controlling the duration of time during which the light is emitted, for example by using Pulse Wave Modulation (PWM) techniques.

It will be understood that, as used herein, the term "light" may refer to energy produced by radiative sources such as electromagnetic radiative sources and may include, for example, any wavelength within the radio, microwave, millimeter wave, infrared, visible, ultraviolet, gamma ray or X-ray spectra. Detector 170 may be chosen to be specifically sensitive to the chosen targeted energy spectrum of light source 160.

In some embodiments, detector 170 may be configured to detect the intensity of light at the red and IR wavelengths. In some embodiments, an array of sensors may be used and each sensor in the array may be configured to detect an intensity of a single wavelength. In operation, light may enter detector 170 after passing through the subject's tissue. Detector 170 may convert the intensity of the received light into an electrical signal. The light intensity may be directly related to the absorbance and/or reflectance of light in the tissue. That is, when more light at a certain wavelength is absorbed or reflected, less light of that wavelength is received from the tissue by detector 170.

After converting the received light to an electrical signal, detector 170 may send the detector signal (e.g., a PPG signal) to PPG monitor 101, where the detector signal may be processed and physiological parameters may be determined. In some embodiments, the detector signal may be preprocessed by sensor 150 before being transmitted to PPG monitor 101. In some embodiments, PPG monitor 101 may perform any suitable analog processing of the detector signal using analog processing circuitry 125. The conditioning performed by analog processing circuitry 125 may include any type of filtering (e.g., low pass filtering, high pass filtering, band pass filtering, notch filtering, IIR filtering, FIR filtering, adaptive filtering, or any other suitable filtering), amplifying, performing an operation on the received signal (e.g., taking a derivative, integrating, averaging), performing any other suitable signal conditioning (e.g., converting a current signal to a voltage signal), or any combination thereof. In some embodiments, analog processing circuitry 125 may comprise circuitry for performing filtering operations. Analog processing circuitry 125 may comprise circuitry for adjusting filtering operations. For example, analog processing circuitry may comprise circuitry capable of scaling the signal. In some embodiments analog processing circuitry 125 may comprise circuitry capable of scaling the detector signal between a detected rising and a detected falling edge of the detector signal. Such selective scaling may be used to adjust the analog filtering functionality. In some embodiments, analog processing circuitry 125 may also be configured to perform analog to digital conversion to convert the detector signal from an analog form into a digital form.

In some embodiments, PPG monitor 101 may also be configured to perform any suitable digital processing of the detector signal using digital processing circuitry 130. For example, digital processing circuitry 130 may be configured to process the detector signal after it was converted into digital form by an analog-to-digital conversion (ADC) circuitry. The conditioning performed by digital processing circuitry 130 may include any type of filtering (e.g., Bessel filtering, anti-aliasing filtering, low pass filtering, FIR filtering, IIR filtering, adaptive filtering, or any other suitable filtering), dark subtraction, decimation, performing an operation on the received signal (e.g., taking a derivative, averaging), performing any other suitable signal conditioning, or any combination thereof. In some embodiments, digital processing circuitry 130 may comprise filter 132 for performing filtering operations. Filter 132 may comprise a filter history 134 for storing filter history that may be used by the filter 132 to perform filtering operations. Filtering operations may comprise, among other things, applying filtering coefficients to the detector signal.

In some embodiments, one or more gain levels may be used to adjust the amplification of the detector signal received from detector 170. The gain level may be set by gain controller 142 of PPG monitor 101. In some embodiments, gain controller 142 may be a gain controller. For example, gain controller 142 may control the gain level of analog processing circuitry 125, digital processing circuitry 130, any other element of the PPG monitor 101, or any combination thereof. In some embodiments, gain settings may comprise several discrete gain settings for amplifying the detector signal. For example, 2× gain setting may amplify the detector signal level by a factor of 2, 4× gain setting may amplify the detector signal level by a factor 4, 10× gain setting may amplify the detector signal level by a factor 10, etc.

Although only one detector 170 is depicted in FIG. 1, in some embodiments, sensor 150 may include additional detectors located at different distances from the light source 160. In some embodiments, sensor 150 may send the detector signal to PPG monitor 101 using any kind of wired or wireless connectors suitable for transmitting the detector signal, or any kind of communication of connectors. For example, connectors may comprise a COM port, Ethernet port, wireless port, a proprietary port, any other communication port, or any combination thereof.

In the embodiment shown, PPG monitor 101 may include processor 115. Processor 115 may be configured to determine the power level of light source 160 and the gain level for PPG monitor 101. In some embodiments, the power level and the gain level may be pre-defined. In some embodiments, the power level and the gain level may be determined based on the detector signal. In some embodiments, the power level may be selected to achieve the highest possible signal-to-noise ratio without saturating any element of PPG monitor 101 and while meeting other constraints necessary for operation of PPG monitor 101. In another example, the power level may be increased during certain critical portions of the patient's cardiac cycle. For example, the power level may be increased during the peak and valley of the cardiac cycle, and decreased during rise and fall of the cardiac cycle (e.g., to save energy). In some embodiments, the gain level may be selected to achieve the highest possible signal-to-noise ratio while keeping the detector signal in the operating range of the PPG monitor 101. In some embodiments, the gain level may be selected to prevent saturation of the analog processing circuitry 125. In some embodiments, the power level and the gain level may be determined in any other manner. Once the power level is determined by processor 115, light drive circuitry 140 may generate an appropriate light drive signal based on the determined power level. Once the gain level is determined by processor 115, gain controller 142 may modify the gain level of the elements of PPG monitor 101 to achieve the desired amplification of the detector signal.

In some embodiments, processor 115, may be configured to calculate a scaling factor based on the determined power level and the determined gain level. In some embodiments, the scaling factor may be calculated according to the following equation: $SF=(PL_D*GL_D)$, where SF is the scaling factor, $PL_D$ is the determined power level, and $GL_D$ is the determined gain level. In some embodiments, the scaling factor may also be determined based on the previously set power level and the previously set gain level. For example, the scaling factor may be determined according to the following equation: $SF=(PL_D*GL_D)/(PL_P*GL_P)$, where SF is the scaling factor, $PL_D$ is the determined power level, $GL_D$ is the determined gain level, $PL_P$ is the previously set power level, and $GL_P$ is the previously set gain level. In some embodiments, the scaling factor may be calculated based on the determined power and the determined gain level in any other manner.

In some embodiments, the scaling factor may be used by processor 115 to adjust the filter history or filter coefficients of filter 132. For example, values of the filter history of filter 132 may be scaled by (e.g., multiplied by) the scaling factor. In some embodiments, the filter coefficients of filter coefficients of filter 132 may be scaled by a ratio of a previously determined scaling factor and the newly calculated scaling factor. In some embodiments, both the filter history and the filter coefficients of filter 132 may be adjusted by processor 115. In some embodiments, processor 115 may be configured to use the detector signal that was filtered by filter 132 to determine at least one physiological parameter of the subject. In some embodiments, the detector signal that was filtered by filter 132 may be used to determine at least one physiological parameter of the subject.

In some embodiments, PPG monitor 101 may comprise calibration circuitry 144. Calibration circuitry 144 may be used to calibrate PPG monitor 101 according to the effects of gain controller 142 setting the gain level of PPG monitor 101, and the effect of light drive circuitry 140 setting a power level of light sources 160. For example, calibration circuitry 144 may empirically determine the actual observed gain change of PPG monitor 101 in response to a change in the gain level applied by gain controller 142. For example, calibration circuitry 144 may determine that a change from 2× gain level to 4× gain level results in an actual 2.2 fold increase in the amplitude of the detector signal, instead of a theoretical 2 fold increase. In some embodiments, calibration circuitry 144 may determine actual observed gain change for every possible change in gain levels. For example, calibration circuitry 144 may determine actual gain change for a change from 2× gain level to 4× gain level, from 2× gain level to 8× gain level, from 4× gain level to 8× gain level, etc.

In some embodiments, calibration circuitry 144 may also empirically determine the actual observed change in the intensity of the light produced by light sources 160 in response to a change in the power level applied by light drive circuitry 140. For example, calibration circuitry 144 may determine that a change from 10 mA power level to 40 mA power level results in an actual 3.9 fold increase in the intensity of the light, instead of a theoretical 4 fold increase. In some embodiments, calibration circuitry 144 may determine actual light intensity change for every possible change in power level of light source 160. For example, calibration circuitry 144 may determine the actual light intensity change for a change from 10 mA power level to 20 mA power level, from 10 mA power level to 40 mA power level, from 20 mA power level to 40 mA power level, etc.

In some embodiments, calibration circuitry 144 may perform calibration upon start-up of PPG monitor 101. In some embodiments, calibration circuitry 144 may perform calibration when it is safe to do so. For example, calibration may be performed when psychological parameters of the subject remain stable for a predetermined period of time or when the calibration time is much shorter than the time in which a measurement of interest is likely to change. In some embodiments, calibration may include additional processing, for example calibration may include averaging or outlier rejection (e.g., due to patient movement or blood flow). In some embodiments, calibration circuitry 144 may perform calibration when a user requests the calibration via user interface 110. In some embodiments, calibration circuitry 144 may perform calibration at any other time. In some embodiments, calibration may be performed at a factory. In some embodiments, calibration may be performed using a purpose-made calibration device. In some embodiments, calibration circuitry 144 may generate calibration data to store the results of the calibration and make the calibration data available to processor 115. In some embodiments, calibration data may be stored using non-transitory memory of PPG monitor 101.

In some embodiments, processor 115 may be configured to calculate a scaling factor based on the calibration data in addition to the determined power level and the determined gain level. For example, the scaling factor may be calculated as a predicted change in the light intensity level multiplied by predicted change in the gain level. The predicted changes may be determined by processor 115 based on the previous gain level, previous power level, determined gain level, determined power level, and calibration data. For example, the scaling factor may be determined according to the following equation: $SF=(PL_{pr}*GL_{pr})/(PL_P*GL_P)$, where SF is the scaling factor, $PL_{pr}$ is the predicted power level, $GL_{pr}$ is the predicted gain level, $PL_P$ is the previously set power level, and $GL_P$ is the previously set gain level. Predicted power level value $PL_{pr}$ may be based on a determined power level and calibration data. Predicted gain level value $GL_{pr}$ may be based on a determined gain level and calibration data. In one example, the current gain level is 2× and the new determined gain level is 4×, the current power level is 10 mA, and new determined gain level is also 10 mA. The calibration data may be used to predict that that change from gain level 2× to gain level 4× will result in 1.8 fold increase in the actual gain level. In this example, processor 115 may calculate the scaling factor by multiplying the predicted increase in gain level (1.8) by an expected change in light intensity level (1). In some embodiments, other techniques for calculating the scaling factor based on the determined power level, the determined gain level, and the calibration data may be used. In some embodiments, the scaling of the filter input, filter history, or filter coefficients can be used to minimize the step response produced by the filter after a gain change. In some embodiments, even if an imperfectly calculated scaling factor is used, the step response may be attenuated because an error in the calculated scaling factor may be insignificant compared to the magnitude of the gain change.

Sensor 150 may also include additional components not depicted in FIG. 1. For example, sensor 150 may include an internal power source (e.g., a battery) and a wireless transmitter for communicating with PPG monitor 101. As another example, sensor 150 may include additional sensor components such as, for example, a temperature sensor.

In the embodiment shown, PPG monitor 101 includes user interface 110. User interface 110 may include a user input device, a display, a speaker, a haptic device, a printer, or any other suitable output device. User interface 110 may include, for example, any suitable device or devices such as one or more medical devices (e.g., a medical monitor that displays various physiological parameters, a medical alarm, or any other suitable medical device that either displays physiological parameters or uses the output of processor 115 as an input), one or more display devices (e.g., monitor, personal digital assistant (PDA), mobile phone, tablet computer, any other suitable display device, or any combination thereof), one or more audio devices, one or more memory devices (e.g., hard disk drive, flash memory, RAM, optical disk, any other suitable memory device, or any combination thereof), one or more printing devices, any other suitable output device, or any combination thereof.

User interface 110 may include any type of user input device such as a keyboard, a mouse, a touch screen, buttons, switches, a microphone, a joy stick, a touch pad, or any other suitable input device. The inputs received by user interface 110 can include information about the subject, such as age, weight, height, diagnosis, medications, treatments, and so forth.

In an embodiment, the subject may be a medical subject and user interface 110 may exhibit (e.g., via a display) a list of values which may generally apply to the subject, such as, for example, age ranges or medication families, which the user may select using a user input device. Additionally, user interface 110 may display, for example, an estimate of a subject's blood oxygen saturation, pulse rate information, respiration rate and/or effort information, blood pressure information, hemoglobin concentration information, cardiac output, fluid responsiveness parameters, any other parameters, and any combination thereof. User interface 110 may include any type of display such as a cathode ray tube display, a flat panel display such as a liquid crystal display or plasma display, or any other suitable display device. A speaker of user interface 110 may provide an audible sound that may be used in various embodiments, such as for example, sounding an audible alarm in the event that a subject's physiological parameters are not within a predefined normal range.

Figure 2:
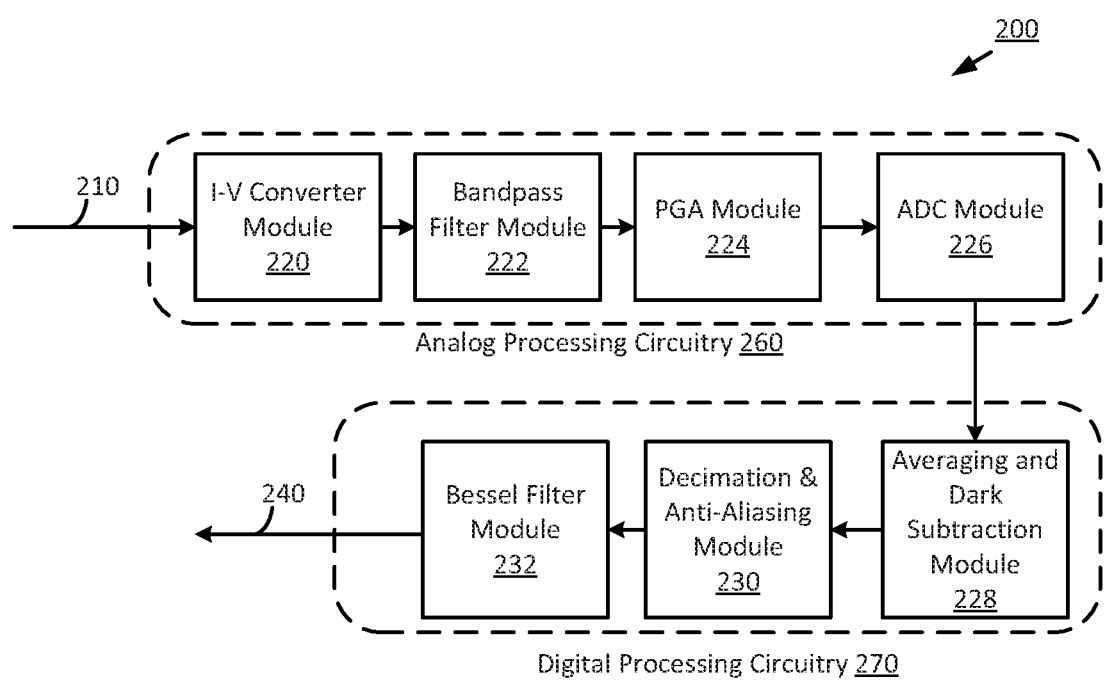
FIG. 2 shows a block diagram of an exemplary analog processing circuitry and exemplary digital processing circuitry with some embodiments of the present disclosure.

FIG. 2 shows a block diagram of a processing circuitry 200 comprising exemplary analog processing circuitry (e.g., analog processing circuitry 125 of FIG. 1) and exemplary digital processing circuitry (e.g., digital processing circuitry 130 of FIG. 1) in accordance with some embodiments of the present disclosure. Processing circuitry 200 may include analog processing circuitry 260 and digital processing circuitry 270.

In some embodiments, analog processing circuitry 260 may be configured to receive detector signal 210. Detector signal 210 may be received from a photodetector (e.g., detector 170 of FIG. 1). In some embodiments, analog processing circuitry 260 may comprise several modules for processing detector signal 210. As used herein, the term "module" may include hardware components (e.g., processor, controller) or a combination of hardware and software components. Analog processing circuitry 260 may comprise I-V converter module 220 configured to perform current to voltage conversion of the detector signal. In some embodiments, I-V converter module 220 may amplify the detector signal in accordance with a determined gain level. Analog processing circuitry 260 may also comprise a bandpass filter module 222 configured to perform bandpass filtering of the detector signal received from I-V converter module 220. Analog processing circuitry 260 may also comprise a Programmable Gain Array (PGA) module 224 configured to amplify the detector signal received from bandpass filter module 222 in accordance with a determined gain level. Analog processing circuitry 260 may also comprise an Analog-to-Digital (ADC) module 226 configured to convert the analog detector signal received from PGA module 224. In some embodiments, ADC module 226 may convert the analog detector signal received from PGA module 224 into a predetermined number of discrete levels (e.g., 65,536 discrete levels). ADC module 226 may be configured to transmit the detector signal to digital processing circuitry 270. It will be understood that analog processing circuitry 260 may also comprise other modules for additional processing of the detector signal. For example, analog processing circuitry 260 may also comprise modules configured to perform low pass filtering, high pass filtering, band pass filtering, notch filtering, IIR filtering, FIR filtering, adaptive filtering, or any other suitable filtering.

In some embodiments, digital processing circuitry 270 may comprise several modules for processing the detector signal. For example, digital processing circuitry 270 may comprise averaging and dark subtraction module 228 configured to subtract detector samples received during periods when LEDs (e.g., light source 160 of FIG. 1) were turned off from detector samples received during periods when LEDs were turned on. In some embodiments, averaging and dark subtraction module 228 may also be configured to average several samples and transmit the result to decimation and anti-aliasing module 230. Decimation and anti-aliasing module 230 may be configured to decimate samples of the detector signal received from averaging and dark subtraction module 228. In some embodiments, decimation and anti-aliasing module 230 may perform anti-aliasing operations on the decimated samples of the detector signal. In some embodiments, decimation and anti-aliasing module 230 may output the detector signal to Bessel filter module 232. Bessel filter module 232 may be configured to perform Bessel filtering of the detector signal. It will be understood that digital processing circuitry 270 may also comprise other modules for additional processing of the detector signal. For example, digital processing circuitry 270 may also comprise modules configured to perform anti-aliasing filtering, low pass filtering, FIR filtering, IIR filtering, adaptive filtering, or any other suitable filtering.

Digital processing circuitry 270 may be configured to output processed detector signal 240. Processed detector signal 240 may then be used to determine at least one physiological parameter. The at least one physiological parameter may comprise at least one of heart rate and oxygen saturation. For example, processed detector signal 240 may be outputted to a processor such as processor 115 of FIG. 1 for determining physiological parameters.

In some embodiments, detector signal 210 may be affected by a determined power level of the LEDs. In some embodiments, one or more modules of the analog processing module may be configured to amplify the detector signal according to a determined gain level. For example, I-V converter module 220 and PGA module 224 may be configured to amplify the detector signal according to the determined gain levels. In some embodiments, one or more modules of digital processing circuitry 270 may comprise at least one of filter history and filter coefficients. For example, bandpass filter module 222 may comprise filter coefficients; decimation and anti-aliasing module 230 may comprise both filter history and filter coefficients used for anti-aliasing operations; and Bessel filter module 232 may comprise a filter history necessary for Bessel filtering.

In some embodiments, a processor may be used to determine a scaling factor based on the determined power level and the determined gain level for processing circuitry 200. The scaling factor may be determined using any of the techniques describe above. In some embodiments, the operation of processing circuitry 200 may be improved by applying the scaling factor to filter history of at least one module of processing circuitry 200. For example, values of the filter history of decimation and anti-aliasing module 230 or Bessel filter module 232 may be multiplied by the scaling factor. In some embodiments, the operation of processing circuitry 200 may be improved by applying the scaling factors to filter coefficients of at least one module of processing circuitry 200. For example, filter coefficient values of the bandpass filter module 222 may be multiplied by the scaling factor. In some embodiments, filter history and coefficients may be adjusted based on the scaling factor in any other manner.

In some embodiments, adjusting the filter history or the filter coefficients may improve the determination of physiological parameters from processed detector signal 240. For example, the change in the LED power level or a change in the gain level may create filter artifacts. For example, it is possible that due to a change in LED power level or a change in the gain level, the filters will, for some time, operate on a buffer (e.g., filter history) that contains detector samples that were acquired at different gain levels, thus creating undesirable filter artifacts by simultaneously processing detector samples acquired at different hardware settings. By applying the scaling coefficient to a filter history or to the filter coefficients of at least one module of system 200, filter artifact in the detector signal may be attenuated or removed leading to more accurate determination of physiological parameter. In some embodiments, applying the scaling coefficient to a filter history or to the filter coefficients of at least one module of system 200, may reduce the amount of ringing created by the change in LED power level or a change in the gain level. In some embodiments, applying the scaling coefficient to a filter history or to the filter coefficients of at least one module of system 200 may reduce length of a step response created by the change in LED power level or a change in the gain level.

In some embodiments, digital processing circuitry 270 may operate using floating point arithmetic. When floating point arithmetic is used, it may be possible to normalize all detector level samples to the same level in order to prevent filter artifacts. In some embodiments, digital processing circuitry 270 may operate using fixed point arithmetic where it may be difficult to normalize all detector level samples to the same level without causing saturation or underflow errors in filters. In these embodiments, it may be preferable to scale the filter coefficients instead of normalizing detector level samples. In some embodiments, scaling the filter coefficients instead of normalizing detector level samples may not completely prevent an appearance of step response, however the length of ringing generated by the by the change in LED power level or a change in the gain level may be reduced. For example, it may be typical for a current oximetry system to experience 0.5-0.75 seconds of ringing following a change in change in LED power level or a change in the gain level. However, with coefficient scaling in a fixed point system, the ringing may be reduced to a length smaller than a typical cardiac cycle of a subject.

Additionally, in some embodiments, if the filter history or the filter coefficients of a module are scaled, the subsequent modules of the digital processing circuitry may operate without further scaling because the filter artifact may have already been attenuated, which may reduce or eliminate the need of further compensation or scaling. For example, if the filter history or the filter coefficients of module 228 are scaled, the subsequent modules of the digital processing circuitry 270 (modules 230 and 232) may operate normally without a need for further scaling.

In some embodiments, the scaling factor may be used to adjust functionality of at least one module of analog processing circuitry 260. For example, the functionality of ADC module 226 may be adjusted to scale the detector signal based on the scaling factor. For example, ADC module 226 may be configured to amplify the detector signal by scaling factor between the rising edge and falling edge of the detector signal. By applying such amplification to the detector signal, filter artifact in the detector signal may be attenuated or removed leading to more accurate determination of physiological parameters.

Figure 3A:
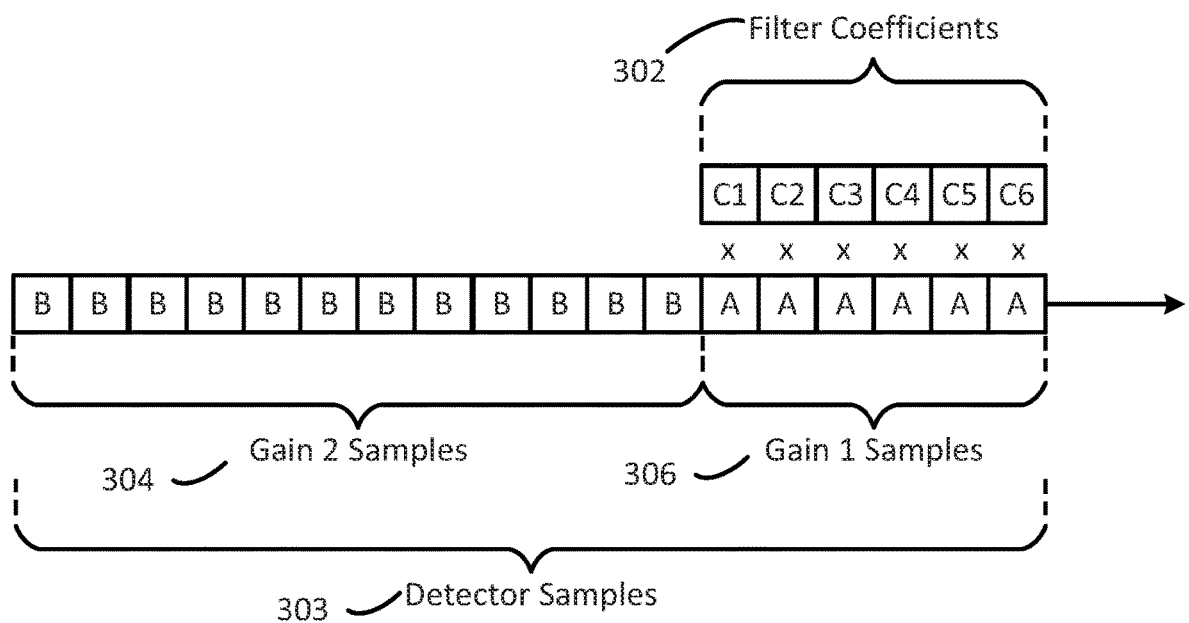
FIGS. 3A, 4A, and 5A show diagrams of several illustrative filtering operations that may be performed by illustrative systems for determining a physiological parameter in accordance with some embodiments of the present disclosure.

FIG. 3A shows a diagram of an illustrative filtering operation that may be performed by a physiological monitoring system (e.g., physiological monitoring system 100 of FIG. 1). For example, the filtering operation illustrated by FIG. 3A may be performed by digital processing circuitry 130 of FIG. 1. It will be understood that FIG. 3A shows a simplified filtering operation for illustrative purposes only, and that any other type of filtering may also be used by the exemplary physiological monitoring systems.

FIG. 3A shows detector samples 303 that are fed through a digital filter. The digital filtering is performed by applying filter coefficients 302 to corresponding detector samples 303. For example, as shown, six values of detector samples 303 may be multiplied by respective values of filter coefficients 302 at a time. The output of the filter may be a combination (e.g., a weighted combination) of the multiplied values. As values of detector samples 303 propagate through the filter, filter coefficients 302 are applied to new values of detector samples 303. In the shown embodiment, gain 1 detector samples 306 labeled as "A" were acquired while the monitoring system was operating at a first gain level (e.g., 1× gain), while gain 2 detector samples 304 labeled as "B" were acquired while the monitoring system was operating at a second, different, gain level (e.g., 2× gain).

Figure 3B:
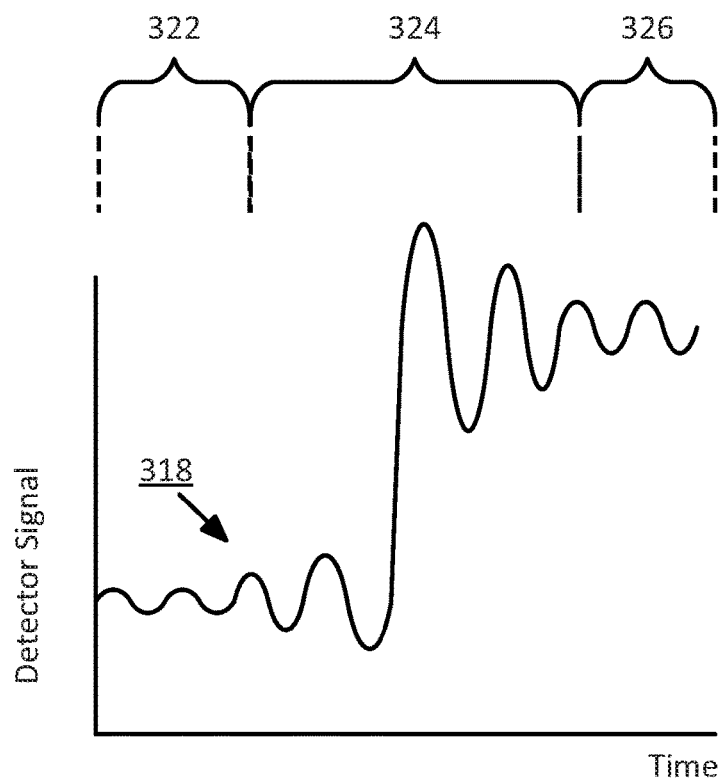
FIGS. 3B, 4B, and 5B show illustrative detector signals that may be generated by illustrative systems for determining a physiological parameter while performing filtering operations shown in FIGS. 3A, 4A, and 5A, respectively.

FIG. 3B shows illustrative changes in the detector signal while the filtering illustrated by FIG. 3A is performed. FIG. 3B illustrates an exemplary detector signal in a monitoring system that does not implement filter history scaling or filter coefficient scaling techniques. FIG. 3B illustrates an exemplary level of detector signal 318 (e.g., a PPG signal) plotted against time during filtering operation illustrated by FIG. 3A. It will be understood that the appearance of the detector signal is simplified for illustrative purposes.

During period 322, the monitoring system filters gain 1 detector samples 306 that were acquired at a first gain level (1× gain). During period 324, the monitoring system is filtering both gain 1 detector samples 306 that were acquired at the first gain level (1× gain) and gain 2 detector samples 304 that were acquired at the second gain level (2× gain). In this illustrative example, detector signal 318 experiences a significant increase in the baseline due to the change in the power level of the light sources. The AC amplitude of detector signal 318 also increases. In addition, because the monitoring system is simultaneously filtering detector samples that were acquired at different gain levels (i.e., gain 1 detector samples 306 and gain 2 detector samples 304), a filtering artifact is generated in detector signal 318. The filtering artifact may, for example, comprise rapid changes in the amplitude of detector signal 318 before detector signal 318 settles at the end of period 324. The filter artifact may negatively affect the monitoring system's determination of physiological parameters based on detector signal 318. During period 326, the filtering artifact is no longer present and the monitoring system is filtering gain 2 detector samples 304 that were acquired only at the second gain level (2× gain). During period 326, the detector signal 318 has settled at a new higher baseline level with increased AC amplitude.

Figure 4A:
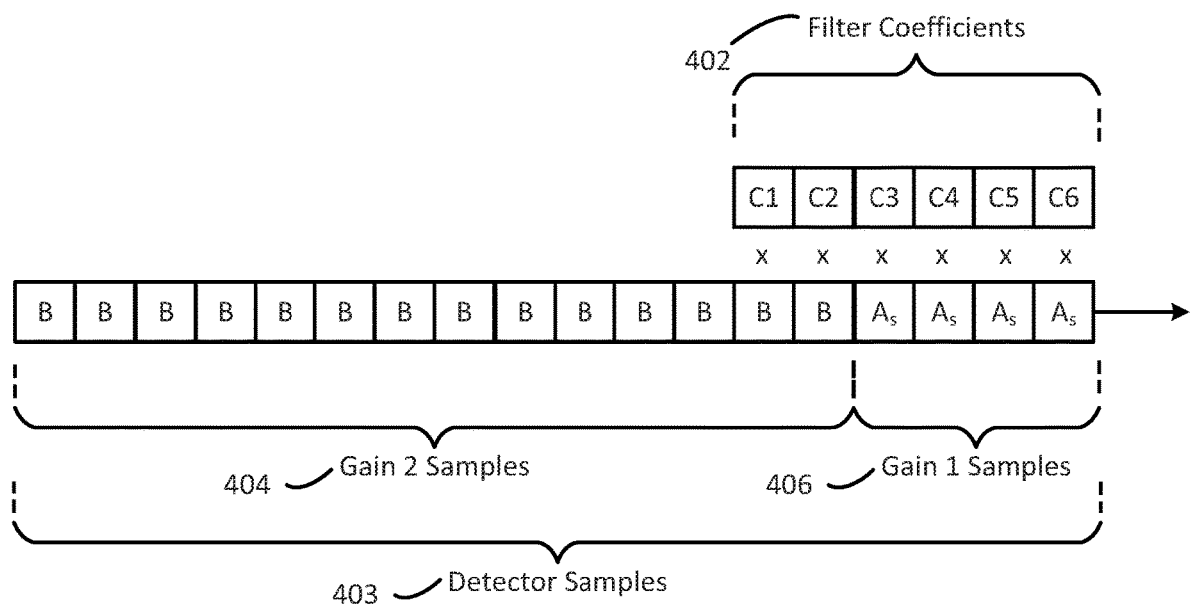

FIG. 4A shows a diagram of an illustrative filtering operation that may be performed by a physiological monitoring system (e.g., physiological monitoring system 100 of FIG. 1). For example, the filtering operation illustrated by FIG. 4A may be performed by digital processing circuitry 130 of FIG. 1. It will be understood that FIG. 4A shows a simplified filtering operation for illustrative purposes only, and that any other type of filtering may also be used by the exemplary monitoring system.

FIG. 4A shows detector samples 403 that are fed through a digital filter that implements filter history scaling according to various embodiments of the present disclosure. The digital filtering is performed by applying filter coefficients 402 to corresponding detector samples 403. For example, as shown, six values of detector samples 403 may be multiplied by respective values of filter coefficients 402 at a time. The output of the filter may be a combination (e.g., a weighted combination) of the multiplied values. As values of the detector samples 403 propagate through the filter, filter coefficients 402 are applied to new values of detector samples 403. In the shown embodiment, gain 1 detector samples 406 labeled as "$A_S$" were acquired while the monitoring system was operating at a first gain level (e.g., 1× gain), while gain 2 detector samples 404 labeled as "B" were acquired while the monitoring system was operating at a second, different, gain level (e.g., 2× gain). In the shown exemplary embodiment, when new gain 2 detector samples 404 that were acquired at gain level 2× reach the filter, old gain 1 detectors samples 406 that were acquired at gain level 1× and that are still being operated on by the filter are scaled. For example, the values of gain 1 detector samples 406 may be multiplied by two to scale the old values to the gain level of the new samples.

Figure 4B:
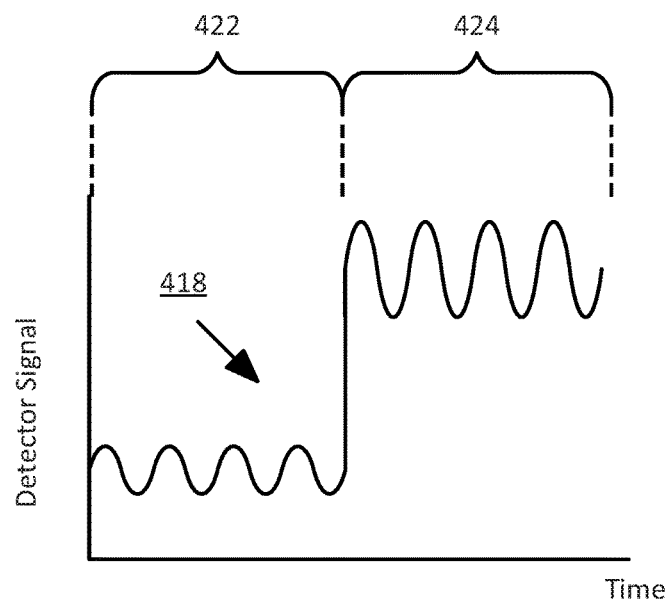

FIG. 4B shows illustrative changes in the detector signal while the filtering illustrated by FIG. 4A is performed. FIG. 4B illustrates an exemplary detector signal 418 in a monitoring system that implements filter history scaling disclosed in the various embodiments of this disclosure. FIG. 4B illustrates an exemplary level of detector signal 418 (e.g., a PPG signal) plotted against time during filtering operation illustrated by FIG. 4A. It will be understood that the appearance of the detector signal is simplified for illustrative purposes.

During period 422, the monitoring system filters gain 1 detector samples 406 that were acquired at a first gain level (1× gain). During period 424, the monitoring system starts to also filter gain 2 detector samples 404 that were acquired at the second gain level (2× gain). However, old gain 1 detector samples 406 that are still being operated on by the filter are scaled prior to application of the filter coefficients 402. In this illustrative example, detector signal 418 experiences an abrupt jump in the baseline level due to the increase in gain level. However, due to the filter history scaling no filter artifact is generated between time period 422 and time period 424. Consequently, detector signal 418 may be used by the monitoring system to determine physiological parameters with increased accuracy.

Figure 5A:
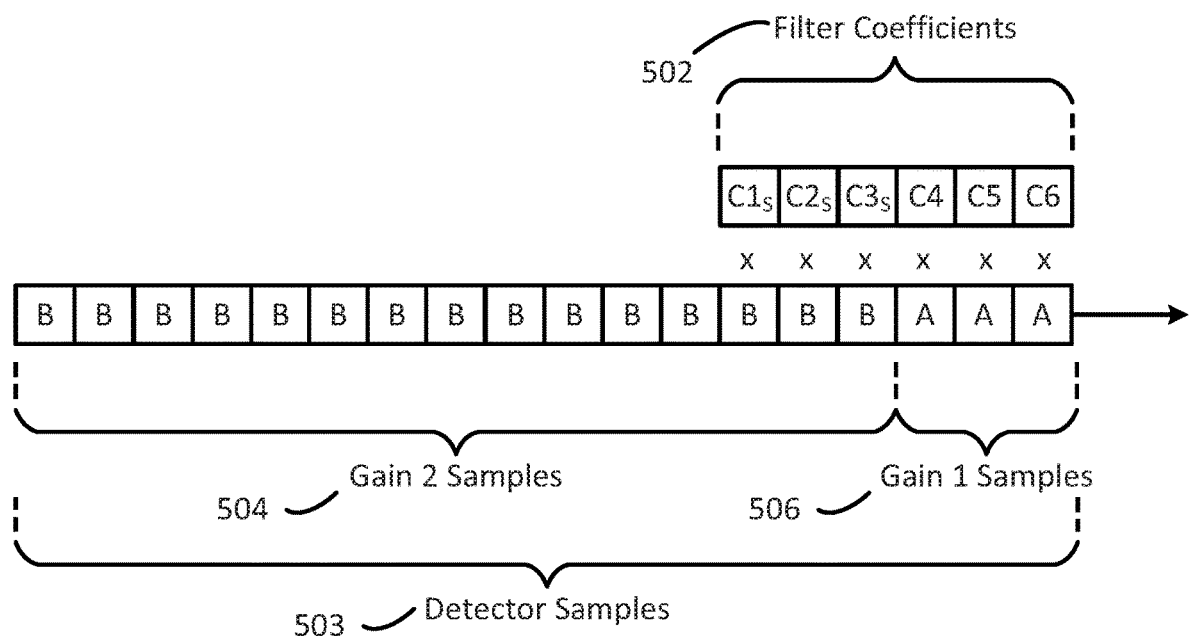

FIG. 5A shows a diagram of an illustrative filtering operation that may be performed by a physiological monitoring system (e.g., physiological monitoring system 100 of FIG. 1). For example, the filtering operation illustrated by FIG. 5A may be performed by digital processing circuitry 130 of FIG. 1. It will be understood that FIG. 5A shows a simplified filtering operation for illustrative purposes only, and that any other type of filtering may also be used by the exemplary physiological monitoring system.

FIG. 5A shows detector samples 503 that are fed through a digital filter that implements filter coefficient scaling according to various embodiments of the present disclosure. The digital filtering is performed by applying filter coefficients 502 to corresponding detector samples 503. For example, as shown, six values of detector samples 503 may be multiplied by respective values of filter coefficients 502 at a time. The output of the filter may be a combination (e.g., a weighted combination) of the multiplied values. As values of detector samples 503 propagate through the filter, filter coefficients 502 are applied to new values of detector samples 503. In the shown embodiment, gain 1 detector samples 506 labeled as "A" were acquired while the monitoring system was operating at a first gain level (e.g., 1× gain), while gain 2 detector samples 504 labeled as "B" were acquired while the monitoring system was operating at a second, different, gain level (e.g., 2× gain). In the shown embodiment, when new gain 2 detector samples 504 (that were acquired at a second gain level) reach the filter, filter coefficients 502 may be scaled. For example, some of the filter coefficients 502 may be divided by two to ensure that the output of the filter remains on same level while detector samples acquired at different gain levels are being propagated though the filter. In some embodiments, filter coefficients 502 may be scaled sequentially, as gain 2 detector samples 504 propagate through the filter. For example, FIG. 5A illustrates filter coefficients 502 being applied to a mix of gain 1 detector samples 506 and gain 2 detector samples 504. Consequently, filter coefficients C4, C5, and C6 that are applied to gain 1 detector samples 506 remain unscaled, while filter coefficients $C1_S$, $C2_S$, and $C3_S$ that are applied to gain 2 detector samples 504 are scaled to counteract the change in gain level from 1× to 2×. When gain 2 detector samples 504 are propagated further, coefficient C4 may be scaled next, followed by coefficient C5, and so on.

Figure 5B:
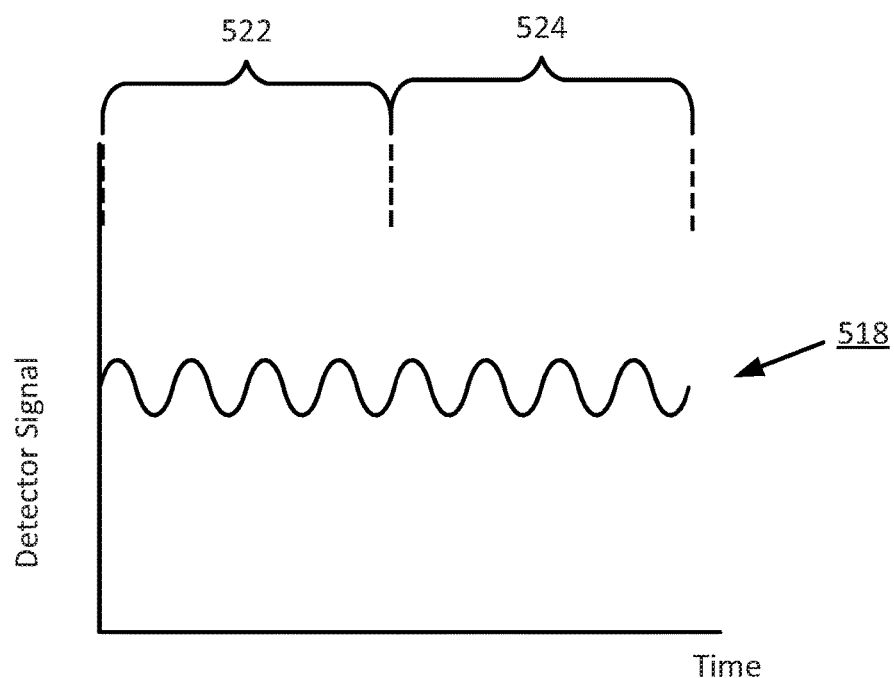

FIG. 5B shows illustrative changes in the detector signal while the filtering illustrated by FIG. 5A is performed. FIG. 5B illustrates an exemplary detector signal 518 in a monitoring system that implements filter history scaling. FIG. 5B illustrates an exemplary level of detector signal 518 (e.g., a PPG signal) plotted against time during filtering operation illustrated by FIG. 5A. It will be understood the appearance of the detector signal is simplified for illustrative purposes.

During period 522, the monitoring system filters gain 1 detector samples 506 that were acquired at a first gain level (1× gain). During period 524, the monitoring system starts to also filter gain 2 detector samples 504 that were acquired at the second gain level (2× gain). However, filter coefficients 502 are being gradually scaled in a manner described above. In this illustrative example, detector signal 518 does not experience a jump in the baseline level because the increase in the gain level is counteracted by the scaling of filter coefficients 502. The AC amplitude of detector signal 518 also remains the same during time period 524. Additionally, due to the filter coefficient scaling no filter artifact is generated between time period 522 and time period 524. Consequently, detector signal 518 may be used by the monitoring system to determine physiological parameters with increased accuracy.

It will be understood that foregoing techniques illustrated by FIGS. 3A, 3B, 4A, 4B, 5A, and 5B are exemplary and that any suitable filter coefficient scaling, filter history scaling, or any combination thereof that is based on changes in the light detection gain levels, changes in the power level of the light sources, or any combination thereof may also be used to eliminate or attenuate a filtering artifact. It will also be understood that filter scaling described above may be implemented in any kind of a digital filter, analog filter, or a combination thereof. In some embodiments, filter scaling described above may be implemented on several filters of a system. In some embodiments, filter scaling described above may be applied to the first digital filter of a system that may create a filtering artifact when a change occurs in the gain setting or in the lights sources power level. In some embodiments, applying filter scaling to the first digital filter of a system may reduce or eliminate the need to apply filter scaling to subsequent filters of the system.

Figure 6:
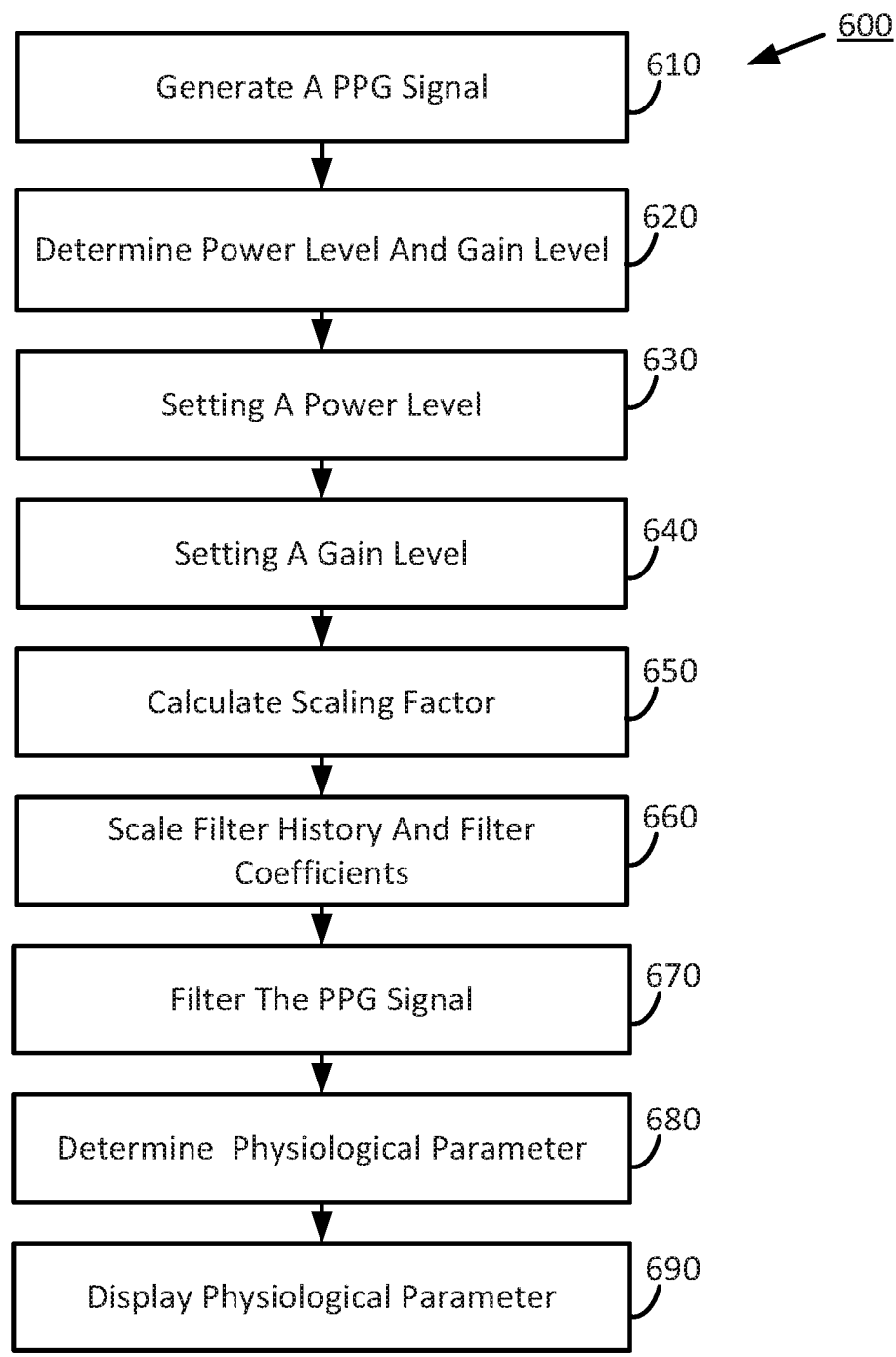
FIG. 6 shows an illustrative flow diagram including steps for determining a physiological parameter in accordance with some embodiments of the present disclosure.

FIG. 6 shows an illustrative flow diagram including steps 600 for determining and applying a scaling factor. Steps 600 of FIG. 6 may be carried out by one or more components of a physiological monitoring system (e.g., system 100 of FIG. 1). In some embodiments, steps 600 of FIG. 5 may be carried out by a pulse oximeter.

Step 610 may include the physiological monitoring system receiving a detector signal (e.g., a PPG signal) from a sensor that is communicatively attached to the physiological monitoring system. In some embodiments, the sensor may be configured to generate a detector signal based on a detected intensity of light at red and IR wavelengths emitted by a light source of the sensor, after the light is attenuated by a tissue of a subject. In some embodiments, the sensor may be sensor 150 of FIG. 1.

Step 620 may include the physiological monitoring system determining a new power level and/or a new detector gain level. In some embodiments, power level and gain level may be determined using aforementioned techniques. In some embodiments, when the monitoring system determines a new power level and/or a new detector gain level the system may blank one or more potentially invalid samples of the detector signal. For example, sample blanking may be performed due to the output of the system being potentially invalid or saturated following a change in the gain level or in the power level. In some embodiments, previous detector samples may be duplicated and substituted in place of the blanked samples. In other embodiment, the blanked samples may be interpolated based on old samples and future samples, as future samples become available.

Step 630 may include the physiological monitoring system setting a power of a light source of the sensor. In some embodiments, the power level settings may correspond to specific voltages provided to the light source of the sensor or to specific current amounts provided to the light source of the sensor. In some embodiments, the power levels may comprise 4,096 discrete levels of current in the range between 0 to 50 mA.

Step 640 may include the physiological monitoring system setting a gain level of the monitoring system (e.g., using a gain controller). In some embodiments, gain settings may comprise several discrete gain settings for amplifying the detector signal. For example, 2× gain setting may amplify the signal level by a factor of 2, 4× gain setting may amplify the signal level by a factor 4, 10× gain setting may amplify the signal level by a factor 10, etc.

Step 650 may include the physiological monitoring system determining a scaling factor. In some embodiments, the scaling factor may be determined based on the determined power level and the determined gain level. In some embodiments, the scaling factor may be calculated according to the following equation: $SF=(PL_D*GL_D)$, where SF is the scaling factor, $PL_D$ is the determined power level, and $GL_D$ is the determined gain level. In some embodiments, the scaling factor may also be determined based on the previously set power level and the previously set gain level. For example, the scaling factor may be determined according to the following equation: $SF=(PL_D*GL_D)/(PL_P*GL_P)$, where SF is the scaling factor, $PL_D$ is the determined power level, $GL_D$ is the determined gain level, $PL_P$ is the previously set power level, and $GL_P$ is the previously set gain level. In some embodiments, the scaling factor may be calculated by the monitoring system based on the determined power level and the determined gain level in any other manner. For example, the scaling factor may be calculated based on calibration data in accordance with the embodiments described above.

Step 660 may include the physiological monitoring system scaling a filter history or filter coefficients of at least one filter of the monitoring system. For example, values of the filter history may be scaled by the value of the scaling factor (e.g., by multiplying the values of the filter history by the value of the scaling factor). In another example, values of the filter coefficients may be scaled by the value of the scaling factor (e.g., by dividing the values of the filter history by the value of the scaling factor). In some embodiments, values of the filter coefficients may be scaled sequentially or gradually as new detector samples propagate through the filter. In some embodiments, the filter history or the filter coefficients may be adjusted based on the calculated scaling factor in any other manner. The physiological monitoring system may then begin filtering the detector signal using a filter with scaled filter history or filter coefficients.

Step 670 may include the physiological monitoring system performing filtering of the detector signal. In some embodiments, filtering may be performed by analog processing circuitry, by digital processing circuitry, or by any combination thereof. Filtering may include low pass filtering, high pass filtering, band pass filtering, notch filtering, IIR filtering, FIR filtering, adaptive filtering, Bessel filtering, any other suitable filtering, or any combination thereof. In some embodiments, one or more filters may comprise a filter history. In some embodiments, the filter history may be used by the filters to filter the detector signal. In some embodiments, one or more filters may comprise filter coefficients. Filtering may be performed by applying the filter coefficients to the detector signal to produce a filtered detector signal.

Step 680 may include the physiological monitoring system determining at least one physiological parameter based on the detector signal that is filtered using a filter with a scaled filter history or filter coefficients. For example, the physiological monitoring system may use the detector signal that was filtered using a filter with a scaled filter history or with scaled coefficients to determine: pulse rate, oxygen situation, blood pressure information, hemoglobin concentration information, cardiac output, fluid responsiveness parameters, any other parameter, or any combination thereof. For example, the physiological monitoring system may determine arterial blood oxygen saturation using two wavelengths of light and a ratio-of-ratios calculation. As another example, the physiological monitoring system may determine regional blood oxygen saturation using two wavelengths of light and two detectors located at different distances from the emitters.

Step 690 may include the physiological monitoring system displaying the at least one determined physiological parameter using, for example, the user interface of the monitoring system. The user interface may include any type of display such as a cathode ray tube display, a flat panel display such as a liquid crystal display or plasma display, or any other suitable display device. In some embodiments, a speaker of user interface may provide an audible sound that may be used in various embodiments, such as for example, sounding an audible alarm in the event that a subject's physiological parameters are not within a predefined normal range.

It will be understood that the aforementioned techniques are not limited to PPG systems, and may be applied to any suitable signal processing in any suitable system. The foregoing is merely illustrative of the principles of this disclosure and various modifications may be made by those skilled in the art without departing from the scope of this disclosure. The above described embodiments are presented for purposes of illustration and not of limitation. The present disclosure also can take many forms other than those explicitly described herein. Accordingly, it is emphasized that this disclosure is not limited to the explicitly disclosed methods, systems, and apparatuses, but is intended to include variations to and modifications thereof, which are within the spirit of the following claims.

What is claimed:

1. A system for determining a physiological parameter of a subject, the system comprising:

a pulse oximetry sensor that generates a photoplethysmography (PPG) signal responsive to detecting light attenuated by the subject;

a gain controller for setting a light detection gain level;

a filter for filtering the PPG signal, wherein the filter comprises at least one of a filter history and filter coefficients;

a processor for:
- determining at least one of a power level of one or more light sources of the pulse oximetry sensor and the light detection gain level;
- calculating a scaling factor based on at least one of the determined power level and the determined light detection gain level, wherein calculating the scaling factor comprises calculating the scaling factor by multiplying the determined power level and the determined light detection gain level;
- scaling the at least one of a filter history and filter coefficients using the scaling factor, wherein scaling comprises scaling the filter history by a ratio of the calculated scaling factor and a previous scaling factor; and
- determining the physiological parameter based on the PPG signal that was filtered by the filter; and a display configured to display the physiological parameter of the subject.

2. The system of claim 1, wherein determining the power level comprises determining the power level to repetitively increase the power level during a portion of cardiac cycle of the subject.

3. The system of claim 1, further comprising the processor for:
- determining a calibration relationship between the light detection gain level determined by the processor and actual observed light detection gain of the system; and
- calculating the scaling factor based on the calibration relationship.

4. The system of claim 3, wherein determining the calibration relationship comprises determining the calibration relationship during start-up of the system.

5. The system of claim 3, wherein determining the calibration relationship comprises determining the calibration relationship when the physiological parameter is determined to be stable.

6. The system of claim 1, wherein scaling the filter coefficients comprises sequentially scaling the filter coefficients based on propagation of the PPG signal through the filter.

7. The system of claim 1, wherein the filter is configured to perform at least one of sample decimation filtering, Bessel filtering, and anti-aliasing filtering.

8. The system of claim 1, wherein the physiological parameter comprises at least one of pulse rate and oxygen saturation.

9. The system of claim 1, wherein the scaling one or more of the filter history and the filter coefficients attenuates a filtering artifact.

10. The system of claim 1, wherein the filter history is stored in a non-transitory memory of the filter.

11. The system of claim 1, wherein the system comprises at least one of a programmable gain array, a current-to-voltage converter, and an analog-to-digital converter configured to amplify the PPG signal.

12. The system of claim 11, wherein the gain controller controls amplification of the at least one of the programmable gain array, the current-to-voltage converter, and the analog-to-digital converter according to the determined light detection gain level.

13. The system of claim 1, wherein the system comprises at least one analog filter for filtering the PPG signal.

14. The system of claim 13, further comprising the processor for adjusting the analog filter based on at least one of the determined power level and the determined light detection gain level.

15. The system of claim 14, wherein one or more light sources of the pulse oximetry sensor is configured to receive power and receives power according to the determined power level.

16. The system of claim 1, wherein the system comprises an output port for communicating the physiological parameter to a non-transitory storage device.

17. A method for determining a physiological parameter of a subject using a pulse oximeter, the method comprising:
- generating, using a pulse oximetry sensor, a photoplethysmography (PPG) signal, wherein the pulse oximetry sensor is configured to detect light attenuated by the subject;
- setting a light detection gain level, using a gain controller;
- filtering the PPG signal, using a filter, wherein the filter comprises at least one of filter history and filter coefficients;
- determining, using a processor of the pulse oximeter, at least one of a power level and the light detection gain level;
- calculating, using the processor of the pulse oximeter, a scaling factor based on at least one of the determined power level and the determined light detection gain level, wherein calculating the scaling factor comprises calculating the scaling factor by multiplying the determined power level and the determined light detection gain level;
- scaling, using the processor of the pulse oximeter, the at least one of a filter history and filter coefficients using the scaling factor, wherein scaling comprises scaling the filter history by a ratio of the calculated scaling factor and a previous scaling factor;
- determining, using the processor of the pulse oximeter, the physiological parameter based on the PPG signal that was filtered by the filter; and
- displaying, using a display of the pulse oximeter, the physiological parameter of the subject.

18. The method of claim 17, further comprising:
- determining, using the processor of the pulse oximeter, a calibration relationship between the light detection gain level determined by the processor of the pulse oximeter and actual observed light detection gain of the pulse oximeter; and
- calculating, using the processor of the pulse oximeter, a scaling factor based on the calibration relationship.

* * * * *